(12) United States Patent
Kim

(10) Patent No.: US 9,744,201 B2
(45) Date of Patent: Aug. 29, 2017

(54) RED GINSENG SAPONIN EXTRACT AND METHOD FOR PREPARING THE SAME

(71) Applicant: Sun-sug Kim, Gangneung-si (KR)

(72) Inventor: Sun-sug Kim, Gangneung-si (KR)

( * ) Notice: Subject to any disclaimer, the term of this patent is extended or adjusted under 35 U.S.C. 154(b) by 128 days.

(21) Appl. No.: 14/923,696

(22) Filed: Oct. 27, 2015

(65) Prior Publication Data

US 2016/0143973 A1    May 26, 2016

(30) Foreign Application Priority Data

Nov. 25, 2014 (KR) ........................ 10-2014-0164889

(51) Int. Cl.
*A61K 36/254* (2006.01)
*A61K 36/258* (2006.01)

(52) U.S. Cl.
CPC ........ *A61K 36/258* (2013.01); *A61K 2236/00* (2013.01)

(58) Field of Classification Search
None
See application file for complete search history.

(56) References Cited

FOREIGN PATENT DOCUMENTS

| KR | 10-0797016 | 1/2008 |
|----|------------|--------|
| KR | 10-2010-0005828 | 1/2010 |
| KR | 10-1095357 | 12/2011 |
| KR | 10-1151722 | 6/2012 |
| KR | 10-2013-0054577 | 5/2013 |
| KR | 10-2013-0085935 | 7/2013 |

*Primary Examiner* — Chris R Tate
*Assistant Examiner* — Russell Fiebig
(74) *Attorney, Agent, or Firm* — Kile Park Reed & Houtteman PLLC

(57) ABSTRACT

Disclosed is a method for preparing a red ginseng saponin extract. In the method, saponin components and non-saponin components are extracted from red ginseng and the non-saponin components are selectively removed from the red ginseng extract to prepare a red ginseng extract containing large amounts of the saponin components. According to the method, saponin components are extracted from red ginseng in high yield and non-saponin components are efficiently removed from the extract. Also disclosed is a red ginseng saponin extract prepared by the method. The red ginseng saponin extract is free of precipitable substances and putrefactive substances, such as starch and free sugars, and contains high-purity saponin components at high concentrations. The red ginseng saponin extract is prevented from being discolored and precipitated even after long-term storage, achieving good storage stability and high marketability.

7 Claims, 15 Drawing Sheets

FIG. 6

ANALYTICAL REPORT

| Center of eco-friendly bioindustry | Leader in quality assurance based on advanced food science and technology | Jeonnam Biofood Technology Center |
|---|---|---|

Issue No.: Reference-1307-074  
Receipt No. : 1307-02-043

| Product Name | Culduct Public | | | Received on | July 17, 2013 |
|---|---|---|---|---|---|
| Food type | - | Test purpose | For reference | Finished on | July 23, 2013 |
| Zip code | 548-853 | Address | Jandeok-ri, Donggang-myeon, Koheung-gun, Jeonbuk | Detailed address | 1121-3 (Enjoy Natural) |
| Requested from | Culduct | Representative | KIM Sun-sug | Requested by | KIM Sun-sug |
| Shelf life | - | Manufactured on | - | Received by | SO Seon-nyeo |
| Test Items and Results | | | | | |
| Test Item | Unit | | Result | | Remarks |
| Rg1 | -(mg/g) | | 4.0106 | | - |
| Rb1 | -(mg/g) | | 28.3127 | | - |
| Rg3 | -(mg/g) | | 0.7982 | | - |
| Judgment : -    Operator : SO Seon-nyeo<br>       Persons in charge : YOON Su-kyeong、SONG Hyeon-woo、SHIN Chang-sik<br>Remarks : This report provides the results of analysis on the requested test items of a sample submitted by the client and cannot be used for product advertisement, commercial applications, and legal settlements other than the requested purpose.<br><br>* The judgment is limited to the requested test items only. | | | | | |
| I hereby issue the above analytical report.<br>July 23, 2013<br>Jeonnam Bioindustry Foundation<br>Biofood Technology Center  Director | | | | | |

520-330 , Mt. 15-1, Dongsu-dong, Naju-si, Jeollanamdo    TEL : 061-336-9620    FAX : 061-336-9627

FIG. 7

ANALYTICAL REPORT

| Center of eco-friendly bioindustry | | Leader in quality assurance based on advanced food science and technology | | Jeonnam Biofood Technology Center | |
|---|---|---|---|---|---|

Issue No. : Reference-1307-075  Receipt No. : 1307-02-044

| Product Name | Culduct Divided | | | Received on | July 17, 2013 |
|---|---|---|---|---|---|
| Food type | - | Test purpose | For reference | Finished on | July 23, 2013 |
| Zip code | 548-853 | Address | Jandeok-ri, Donggang-myeon, Koheung-gun, Jeonbuk | Detailed address | 1121-3 (Enjoy Natural) |
| Requested from | Culduct | Representative | KIM Sun-sug | Requested by | KIM Sun-sug |
| Shelf life | - | Manufactured on | - | Received by | SO Seon-nyeo |
| Test Items and Results | | | | | |
| Test Item | Unit | | Result | | Remarks |
| Rg1 | -(mg/g) | | 4.4604 | | - |
| Rb1 | -(mg/g) | | 30.7846 | | - |
| Rg3 | -(mg/g) | | 0.9290 | | - |

Judgment : -    Operator : SO Seon-nyeo

Persons in charge : YOON Su-kyeong, SONG Hyeon-woo, SHIN Chang-sik

Remarks : This report provides the results of analysis on the requested test items of a sample submitted by the client and cannot be used for product advertisement, commercial applications, and legal settlements other than the requested purpose.

* The judgment is limited to the requested test items only.

I hereby issue the above analytical report.

July 23, 2013

Jeonnam Bioindustry Foundation
Biofood Technology Center  Director

520-330,  Mt. 15-1, Dongsu-dong, Naju-si, Jeollanamdo TEL : 061-336-9620   FAX : 061-336-9627

FIG. 8

ANALYTICAL REPORT

| Center of eco-friendly bioindustry | Leader in quality assurance based on advanced food science and technology | | | Jeonnam Biofood Technology Center | |
|---|---|---|---|---|---|
| Issue No. : Reference-1403-060 | | | | Receipt No. : 1403-02-071 | |
| Product Name | culduct redginseng basic | | | Received on | March 18, 2014 |
| Food type | - | Test purpose | For reference | Finished on | March 25, 2014 |
| Zip code | 200-701 | Address | Jumunjin-eup, Kangreung-si, Kangwaon-do | Detailed address | 1110, Business Incubation Center, Kangwon Provincial College |
| Requested from | culduct | Representative | KIM Sun-sug | Requested by | KIM Sun-sug |
| Shelf life | - | Manufactured on | - | Received by | SO Seon-nyeo |
| Test Items and Results | | | | | |
| Test Item | Reference value (Unit) | | Result | | Remarks |
| Rg1 | -(mg/g) | | 4.5094 | | - |
| Rb1 | -(mg/g) | | 40.7237 | | - |
| Rg3 | -(mg/g) | | 1.8069 | | - |

Judgment : -       Operator : SO Seon-nyeo

Persons in charge : SONG Hyeon-woo, SHIN Chang-sik

Remarks : This report provides the results of analysis on the requested test items of a sample submitted by the client and cannot be used for product advertisement, commercial applications, and legal settlements other than the requested purpose.

* The judgment is limited to the requested test items only.

I hereby issue the above analytical report.

March 26, 2014

Jeonnam Bioindustry Foundation
Biofood Technology Center  Director

520-330 , 30-5, Dongsunonggongdanji-gil, Naju-si, Jeollanamdo   TEL : 061-336-9620    FAX : 061-336-9627

FIG. 9

ANALYTICAL REPORT

| Center of eco-friendly bioindustry | Leader in quality assurance based on advanced food science and technology | | Jeonnam Biofood Technology Center | |

Issue No. : Reference-1405-002  Receipt No. : 1404-02-058

| Product Name | culduct redginseng ER3 | | | Received on | April 29, 2014 |
|---|---|---|---|---|---|
| Food type | - | Test purpose | For reference | Finished on | May 03, 2014 |
| Zip code | 200-701 | Address | Jumunjin-eup, Kangreung-si, Kangwaon-do | Detailed address | 1110, Business Incubation Center, Kangwon Provincial College |
| Requested from | culduct | Representative | KIM Sun-sug | Requested by | KIM Sun-sug |
| Shelf life | - | Manufactured on | - | Received by | SO Seon-nyeo |

| Test Items and Results | | | |
|---|---|---|---|
| Test Item | Reference value (Unit) | Result | Remarks |
| Rg1 | -(mg/g) | 4.4089 | - |
| Rb1 | -(mg/g) | 51.0283 | - |
| Rg3 | -(mg/g) | 2.1253 | - |

Judgment : -    Operator : SO Seon-nyeo

Persons in charge : SONG Hyeon-woo, SHIN Chang-sik

Remarks : This report provides the results of analysis on the requested test items of a sample submitted by the client and cannot be used for product advertisement, commercial applications, and legal settlements other than the requested purpose.

* The judgment is limited to the requested test items only.

I hereby issue the above analytical report.

May 7, 2014

Jeonnam Bioindustry Foundation
Biofood Technology Center  Director

520-330 , 30-5, Dongsunonggongdanji-gil, Naju-si, Jeollanamdo   TEL : 061-336-9620       FAX : 061-336-9627

FIG. 10

ANALYTICAL REPORT

| | | | | | |
|---|---|---|---|---|---|
| Center of eco-friendly bioindustry | | Leader in quality assurance based on advanced food science and technology | | Jeonnam Biofood Technology Center | |
| Issue No. : Reference-1306-0005 | | | | Receipt No. : 1306-02-003 | |
| Product Name | Redginseng 100 | | | Received on | June 03, 2013 |
| Food type | - | Test purpose | For reference | Finished on | June 05, 2013 |
| Zip code | 548-853 | Address | Jandeok-ri, Donggang-myeon, Koheung-gun, Jeonbuk | Detailed address | 1121-3 (Enjoy Natural) |
| Requested from | - | Representative | KIM Sun-sug | Requested by | KIM Sun-sug |
| Shelf life | - | Manufactured on | - | Received by | SO Seon-nyeo |
| Test Items and Results | | | | | |
| Test Item | | Unit | | Result | Remarks |
| Rg1 | | -(mg/g) | | 1.6242 | - |
| Rb1 | | -(mg/g) | | 4.5954 | - |
| Rg3 | | -(mg/g) | | 0.4731 | - |
| Judgment : -           Operator : SO Seon-nyeo<br>                 Persons in charge : YOON Su-kyeong, SONG Hyeon-woo, SHIN Chang-sik<br>Remarks : This report provides the results of analysis on the requested test items of a sample submitted by the client and cannot be used for product advertisement, commercial applications, and legal settlements other than the requested purpose.<br><br>* The judgment is limited to the requested test items only. | | | | | |
| We hereby issue the above analytical report.<br>                                                                                          June 05, 2013<br>Jeonnam Bioindustry Foundation<br>Biofood Technology Center  Director | | | | | |

520-330, Mt. 15-1, Dongsu-dong, Naju-si, Jeollanamdo     TEL : 061-336-9620     FAX : 061-336-9627

FIG. 11

ANALYTICAL REPORT

Center of eco-friendly bioindustry    Leader in quality assurance based on advanced food science and technology    Jeonnam Biofood Technology Center Issue No. : Reference-1306-0006      Receipt No. : 1306-02-004

| Product Name | Redginseng 200 | | | Received on | June 03, 2013 |
|---|---|---|---|---|---|
| Food type | - | Test purpose | For reference | Finished on | June 05, 2013 |
| Zip code | 548-853 | Address | Jandeok-ri, Donggang-myeon, Koheung-gun, Jeonbuk | Detailed address | 1121-3 (Enjoy Natural) |
| Requested from | - | Representative | KIM Sun-sug | Requested by | KIM Sun-sug |
| Shelf life | - | Manufactured on | - | Received by | SO Seon-nyeo |
| Test Items and Results | | | | | |
| Test Item | Unit | | Result | | Remarks |
| Rg1 | -(mg/g) | | 2.5980 | | - |
| Rb1 | -(mg/g) | | 7.0547 | | - |
| Rg3 | -(mg/g) | | 0.7651 | | - |

Judgment : -           Operator : SO Seon-nyeo

Persons in charge : YOON Su-kyeong, SONG Hyeon-woo, SHIN Chang-sik

Remarks : This report provides the results of analysis on the requested test items of a sample submitted by the client and cannot be used for product advertisement, commercial applications, and legal settlements other than the requested purpose.

\* The judgment is limited to the requested test items only.

I hereby issue the above analytical report.

June 05, 2013

Jeonnam Bioindustry Foundation
Biofood Technology Center Director

520-330, Mt. 15-1, Dongsu-dong, Naju-si, Jeollanamdo      TEL : 061-336-9620     FAX : 061-336-9627

FIG. 12

ANALYTICAL REPORT

| Center of eco-friendly bioindustry | Leader in quality assurance based on advanced food science and technology | | Jeonnam Biofood Technology Center | |

Issue No. : Reference-1404-070                                    Receipt No. : 1404-02-037

| Product Name | culduct redginseng nonsaponin | | | Received on | April 15, 2014 |
|---|---|---|---|---|---|
| Food type | - | Test purpose | For reference | Finished on | April 18, 2014 |
| Zip code | 200-701 | Address | Jumunjin-eup, Kangreung-si, Kangwaon-do | Detailed address | 1110, Business Incubation Center, Kangwon Provincial College |
| Requested from | culduct | Representative | KIM Sun-sug | Requested by | KIM Sun-sug |
| Shelf life | - | Manufactured on | - | Received by | SO Seon-nyeo |
| Test Items and Results | | | | | |
| Test Item | Reference value (Unit) | | | Result | Remarks |
| Rg1 | -(mg/g) | | | Not detected | - |
| Rb1 | -(mg/g) | | | Not detected | - |
| Rg3 | -(mg/g) | | | Not detected | - |

Judgment : -                    Operator : SO Seon-nyeo

Persons in charge : SONG Hyeon-woo, SHIN Chang-sik

Remarks : This report provides the results of analysis on the requested test items of a sample submitted by the client and cannot be used for product advertisement, commercial applications, and legal settlements other than the requested purpose.

\* The judgment is limited to the requested test items only.

I hereby issue the above analytical report.

April 21, 2014

Jeonnam Bioindustry Foundation
Biofood Technology Center  Director

520-330 , 30-5, Dongsunonggongdanji-gil, Naju-si, Jeollanamdo    TEL : 061-336-9620    FAX : 061-336-9627

FIG. 13

ANALYTICAL REPORT

| Center of eco-friendly bioindustry | Leader in quality assurance based on advanced food science and technology | Jeonnam Biofood Technology Center |

Issue No. : Reference-1306-0008                             Receipt No. : 1306-02-009

| Product Name | Redginseng 400 | | | Received on | 2013.06.07 |
|---|---|---|---|---|---|
| Food type | - | Test purpose | For reference | Finished on | 2013.06.11 |
| Zip code | 548-853 | Address | Jandeok-ri, Donggang-myeon, Koheung-gun, Jeonbuk | Detailed address | 1121-3 (Enjoy Natural) |
| Requested from | - | Representative | KIM Sun-sug | Requested by | KIM Sun-sug |
| Shelf life | - | Manufactured on | - | Received by | SO Seon-nyeo |
| Test Items and Results | | | | | |
| Test Item | Unit | | Result | | Remarks |
| Rg1 | -(mg/g) | | Not detected | | - |
| Rb1 | -(mg/g) | | 0.2969 | | - |
| Rg3 | -(mg/g) | | Not detected | | - |

Judgment : -            Operator : SO Seon-nyeo

Persons in charge : YOON Su-kyeong, SONG Hyeon-woo, SHIN Chang-sik

Remarks : This report provides the results of analysis on the requested test items of a sample submitted by the client and cannot be used for product advertisement, commercial applications, and legal settlements other than the requested purpose.

\* The judgment is limited to the requested test items only.

I hereby issue the above analytical report.

June 14, 2013

Jeonnam Bioindustry Foundation
Biofood Technology Center Director

520-330, Mt. 15-1, Dongsu-dong, Naju-si, Jeollanamdo    TEL : 061-336-9620    FAX : 061-336-9627

FIG. 14

ANALYTICAL REPORT

| Center of eco-friendly bioindustry | | Leader in quality assurance based on advanced food science and technology | | Jeonnam Biofood Technology Center | |
|---|---|---|---|---|---|
| Issue No. : Reference-1409-050 | | | | Receipt No. : 1409-02-046 | |
| Product Name | culduct R&D Purified sterilized ivory | | | Received on | September 16, 2014 |
| Food type | - | Test purpose | For reference | Finished on | September 22, 2014 |
| Zip code | 200-701 | Address | Yeonju-ro, Jumunjin-eup, Kangreung-si, Kangwaon-do | Detailed address | 270, 1110, Business Incubation Center, Kangwon Provincial College |
| Requested from | culduct | Representative | KIM Sun-sug | Requested by | KIM Sun-sug |
| Shelf life | - | Manufactured on | - | Received by | SO Seon-nyeo |
| Test Items and Results | | | | | |
| Test Item | | Reference value (Unit) | | Result | Remarks |
| Rg1 | | -(mg/g) | | 1.4433 | - |
| Rb1 | | -(mg/g) | | 38.3214 | - |
| Rg3 | | -(mg/g) | | 1.7696 | - |
| Ethanol | | -(%) | | 1.8849 | |
| Judgment : -     Operator : SO Seon-nyeo, SHIN Ji-seon              Persons in charge : YOON Su-kyeong, SONG Hyeon-woo, SHIN Chang-sik Remarks : This report provides the results of analysis on the requested test items of a sample submitted by the client and cannot be used for product advertisement, commercial applications, and legal settlements other than the requested purpose.  * The judgment is limited to the requested test items only. | | | | | |
| I hereby issue the above analytical report.                                                                                            September 24, 2014 Jeonnam Bioindustry Foundation Biofood Technology Center  Director | | | | | |

520-330 , 30-5, Dongsunonggongdanji-gil, Naju-si, Jeollanamdo    TEL : 061-336-9620 FAX : 061-336-9627

FIG. 15

ANALYTICAL REPORT

| Center of eco-friendly bioindustry | Leader in quality assurance based on advanced food science and technology | | | Jeonnam Biofood Technology Center | |
|---|---|---|---|---|---|
| Issue No. : Reference-1402-053 | | | | Receipt No. : 1402-02-055 | |
| Product Name | culduct saponin samdasoo bottle water 500ml 20days 1°C~4°C | | | Received on | February 13, 2014 |
| Food type | - | Test purpose | For reference | Finished on | February 18, 2014 |
| Zip code | 200-701 | Address | Jumunjin-eup, Kangreung-si, Kangwaon-do | Detailed address | 1110, Business Incubation Center, Kangwon Provincial College |
| Requested from | culduct | Representative | KIM Sun-sug | Requested by | KIM Sun-sug |
| Shelf life | - | Manufactured on | - | Received by | SO Seon-nyeo |
| Test Items and Results | | | | | |
| Test Item | | Unit | | Result | Remarks |
| Total content of ginsenosides Rg1, Rb1 and Rb3 | | -(mg/500ml) | | 4.95 | - |
| pH | | - | | 7.527 | - |
| Chromaticity | x value | - | | 0.3137 | - |
| | y value | - | | 0.3316 | - |

Judgment : -  Operator : SO Seon-nyeo

Persons in charge : YOON Su-kyeong, SONG Hyeon-woo, SHIN Chang-sik

Remarks : This report provides the results of analysis on the requested test items of a sample submitted by the client and cannot be used for product advertisement, commercial applications, and legal settlements other than the requested purpose.

\* The judgment is limited to the requested test items only.

I hereby issue the above analytical report.

February 18, 2014

Jeonnam Bioindustry Foundation
Biofood Technology Center Director

520-330, 30-5, Dongsunonggongdanji-gil, Naju-si, Jeollanamdo    TEL : 061-336-9620 FAX : 061-336-9627

RED GINSENG SAPONIN EXTRACT AND METHOD FOR PREPARING THE SAME

BACKGROUND OF THE INVENTION

1. Field of the Invention

The present invention relates to a method for preparing a red ginseng saponin extract in which saponin components and non-saponin components are extracted from red ginseng and the non-saponin components are selectively removed from the red ginseng extract to prepare a red ginseng extract containing large amounts of the saponin components, and a red ginseng saponin extract prepared by the method.

2. Description of the Related Art

Ginseng radix refers to the root of *Panax ginseng* C. A. Meyer, which is a perennial herb belonging to the Araliaceae family. Ginseng radix is classified into fresh ginseng, red ginseng, and white ginseng by their processing methods.

Fresh ginseng is ginseng that is not processed after it has been harvested from the cultivation farm. Fresh ginseng has a high water content of 70 to 80% and is thus difficult to store for a long period of time. White ginseng is prepared by peeling off the bark of fresh ginseng or drying harvested fresh ginseng under natural sunlight or with hot air. White ginseng has an ivory-white or light yellow color. Red ginseng is prepared by washing unpeeled fresh ginseng, followed by a series of steaming and drying processes. Red ginseng is light yellowish-brown or dark red in color.

Ginseng radix has many efficacies, such as enhancement of physical strength and stamina, hematosis, body heat retention, improvement of fatigue resistance, mental stability, and sedation, which are known to be mainly due to the presence of ginseng saponins.

Saponins are classified into three groups according to their chemical structures: protopanaxadiol, protopanaxatriol, and oleanolic acid. It is known that such saponins have great influences on the regulatory systems, such as the central nervous system, the endocrine system, the immune system, and the metabolic system, and as a result, they are very effective in the regulation of body functions, that is, the normalization of physiological functions.

Red ginseng contains glycosides, panacen, polyacetylene compounds, nitrogenous ingredients, flavonoids, vitamin B complex, trace elements, enzymes, antioxidants, organic acids, and amino acids, like fresh ginseng. Particularly, fresh ginseng experiences many chemical modifications, such as saponin modifications, amino acid changes, and browning, during steaming and drying for the preparation of red ginseng. At this time, saponin components, such as ginsenosides Rg2, Rg3, Rh1, and Rh2, which are peculiar to red ginseng and are not found in fresh ginseng, are newly created. Such red ginseng saponins are known to exhibit cancer prevention, cancer cell growth inhibition, hypotensive, brain cell protection, learning ability improvement, antithrombotic, and antioxidant actions, which are responsible for outstanding pharmacological effects of red ginseng.

However, red ginseng is hardened after drying and is thus inconvenient to directly ingest. Red ginseng is usually taken in the form of a water extract. In recent years, red ginseng concentrates have been popularized for their ease of drinking and storage. For these reasons, most red ginseng processed products are currently being distributed in the form of red ginseng concentrates and products containing them.

The content of saponins in a red ginseng extract is indicative of quality of the red ginseng extract and varies depending on various factors for the extraction of red ginseng. Such factors include physical factors, such as extraction solvent, temperature and time, and chemical factors, such as organic acids present in the extract. Even when only one of these factors is changed, the content of saponins in the extract varies greatly.

According to a widely used traditional method for the preparation of a red ginseng extract, red ginseng is generally extracted with water as an extraction solvent at a high temperature of 85 to 90° C. for 24 to 48 hours. However, the long-term treatment with hot water leads to the degradation of saponins as active ingredients of red ginseng, which is affected by organic acids present in the red ginseng during extraction.

In an attempt to solve this degradation problem, extraction of red ginseng with ethanol as an extraction solvent under heating instead of water is proposed. However, the use of ethanol as an extraction solvent leads to low extraction yield compared to the use of water, produces a strong unpleasant smell, such as an earthy smell, and incurs loss of the original flavor of red ginseng.

Many efforts have been made to solve the above problems. For example, Korean Patent No. 1095357 discloses a method for preparing a processed ginseng radix extract including treating ginseng radix with acidic or alkaline electrolyzed water at a temperature of 50 to 80° C., steaming the treated ginseng radix at a temperature of 90 to 120° C. for 0.5 to 15 hours, and extracting the processed ginseng radix with water, a $C_1$-$C_4$ alcohol or a mixed solvent thereof.

According to this method, the treatment of ginseng radix with acidic and/or alkaline electrolyzed water can efficiently increase the contents of ginsenosides Rg2, Rg3, and Rg5 and can prevent side effects caused by the remaining solvent. However, the bitter taste of particles present in the processed ginseng radix or the processed ginseng radix extract causes a feeling of repulsion upon taking. The extraction with water increases the dissolution of starch particles. The starch particles tend to discolor with time, which causes deterioration of marketability of the ginseng radix extract.

Another method for preparing a red ginseng extract is disclosed in Korean Patent No. 1151722. According to this method, alkaline water at a pH of 8.5 to 10.5 is added to red ginseng, the red ginseng is extracted at 65 to 90° C. for 1 to 12 hours, the extraction is repeated 1 to 10 times, the extract is filtered to remove insoluble matter, and the filtrate is sterilized, filtered, and concentrated. Through the series of processing steps, the red ginseng extract has increased contents of ginsenosides Rg1 and Rb1.

The alkaline water has a higher pH than general water and acts as stabilized water that inhibits ingredients of the extract from being changed. The alkaline water suppresses the conversion of ginsenosides present in ginseng radix or red ginseng to ginsenosides Rh1, Rg2, and Rg3, achieving increased contents of ginsenosides Rg1 and Rb1 after extraction.

If the extraction temperature, the extraction time, and the number of times of extraction are less than the lower limits defined above, the extraction yield is lowered. Meanwhile, if the extraction temperature, the extraction time, and the number of times of extraction exceed the upper limits defined above, ginsenosides and other useful physiologically active ingredients are degraded. Although the extraction temperature, the extraction time, and the number of times of extraction are within the respective ranges defined above, the degradation of ingredients proceeds with increasing extraction yield, impeding the extraction of useful ginsenosides in high yield.

Since the particles present in the extract are very fine and exist in a suspended form, they are not sufficiently removed by general separation methods, such as filtration or centrifugation, leaving residue in the final red ginseng extract. The residue is bitter in taste, which deteriorates the marketability of the red ginseng extract, discolors the red ginseng extract during long-term storage, and forms a precipitate, which is a factor deteriorating the storage stability of the red ginseng extract.

Saponin components and non-saponin components coexist in the extract. Non-saponin components are usually present in a larger amount in the red ginseng than saponin components but are not completely separated from saponin components by the method. Therefore, the content of saponins as active ingredients in the final red ginseng extract is lowered and the saponins are slowly degraded by organic acids present in the red ginseng.

Further, Korean Patent Publication No. 2010-0005828 discloses a method for preparing a red ginseng concentrate by which the degradation of saponins during extraction of red ginseng can be minimized. According to this method, red ginseng is extracted with 30% ethanol, edible soda as a neutralizing agent is added to the extract to neutralize organic acids, and the extraction is repeated 4 times at a temperature of 80° C. for 10 hours. The ethanol extraction reduces the amount of starch extracted compared to water extraction and can inhibit the degradation of saponins. The neutralization prevents the degradation of saponins caused by organic acids.

However, when the red ginseng concentrate is filtered, large solid particles present in the concentrate are removed but fine solid particles are not easily removed. As a result, the taste of the red ginseng concentrate is still bitter, the storage stability of the red ginseng concentrate is deteriorated, and the content of saponin components in the red ginseng concentrate is not increased to a high level due to the coexistence with non-saponin components.

Attempts have steadily been made to extract large amounts of saponin components from ginseng radix or red ginseng in high yield. However, none of the attempts have been succeeded in increasing the contents of saponins to satisfactorily high levels. Further, impurities present in red ginseng extracts are difficult to sufficiently remove, and as a result, the red ginseng extracts tend to discolor or precipitate during long-term storage. These problems remain unsolved.

Most commercially available red ginseng extract products are prepared by concentrating red ginseng extracts to high levels or formulating red ginseng extracts into powders or tablets for longer shelf life. However, beverages or liquid preparations containing red ginseng extracts are not yet commercialized.

SUMMARY OF THE INVENTION

The present invention has been made in an effort to solve the above problems, and it is an object of the present invention to provide a method for preparing a red ginseng extract containing saponin components in high purity by extracting saponin components from red ginseng in high yield and removing non-saponin components as much as possible from the extract, and a red ginseng saponin extract prepared by the method.

One aspect of the present invention provides a method for preparing a red ginseng saponin extract, including: mixing 100 parts by weight of red ginseng with 500 to 700 parts by weight of alkaline ionized water at a pH of 10 to 12 and 1200 to 1800 parts by weight of 90 to 99% (v/v) ethanol and extracting the red ginseng at 60 to 75° C. for 15 to 30 hours to prepare a red ginseng extract; allowing the red ginseng extract to stand at −5 to 0° C. for 20 to 96 hours to separate the red ginseng extract into a first supernatant and a first precipitate; concentrating the first supernatant at 50 to 60° C. for 50 to 90 minutes to obtain a first concentrate having a Brix of 55 to 65; mixing 100 parts by weight of the first concentrate with 150 to 250 parts by weight of alkaline ionized water at a pH of 10 to 12 to adjust the Brix to 15 to 25 and mixing the mixture with 1000 to 1500 parts by weight of 90 to 99% (v/v) ethanol to obtain a first mixture; allowing the first mixture to stand at −5 to 5° C. for 20 to 96 hours to fractionate the first mixture into a second supernatant and a second precipitate; and concentrating the second supernatant at 50 to 60° C. for 50 to 90 minutes to obtain a second concentrate having a Brix of 55 to 65.

Preferably, the method further includes: mixing 100 parts by weight of the second concentrate with 150 to 250 parts by weight of alkaline ionized water at a pH of 10 to 12 to obtain a second mixture having a Brix of 15 to 25; allowing the second mixture to stand at −5 to 0° C. for 90 to 110 hours to separate the second mixture into a third supernatant and a third precipitate; mixing 100 parts by weight of the third supernatant with 80 to 120 parts by weight of alkaline ionized water at a pH of 10 to 12 to obtain a third mixture having a Brix of 8 to 12; allowing the third mixture to stand at −5 to 0° C. for 100 to 150 hours to separate the third mixture into a fourth supernatant and a fourth precipitate; mixing 100 parts by weight of the fourth supernatant with 200 to 250 parts by weight of alkaline ionized water at a pH of 10 to 12 to obtain a fourth mixture having a Brix of 1 to 5; and allowing the fourth mixture to stand at −5 to 0° C. for 120 to 160 hours to separate the fourth mixture into a fifth supernatant and a fifth precipitate and collecting the fifth supernatant.

More preferably, the method further include: concentrating the fifth supernatant at 50 to 60° C. for 60 to 95 minutes to obtain a third concentrate having a Brix of 5 to 65; mixing 100 parts by weight of the third concentrate with 350 to 500 parts by weight of 90 to 99% (v/v) ethanol and allowing the mixture at −5 to 0° C. for 45 to 95 hours to separate the mixture into a sixth supernatant and a sixth precipitate; and concentrating the sixth supernatant at 50 to 60° C. for 60 to 95 minutes to obtain a fourth concentrate having a Brix of 8 to 65.

The third concentrate is more preferably obtained by mixing 100 parts by weight of the fifth supernatant with 200 to 250 parts by weight of acidic ionized water at a pH of 5 to 7 to obtain a mixture having a Brix of 1 to 5, allowing the mixture to stand at −5 to 0° C. for 120 to 160 hours to separate the mixture into a supernatant and a precipitate, removing the precipitate, and concentrating the supernatant.

More preferably, the method further includes: mixing the fourth precipitate with the fifth precipitate to obtain a mixed precipitate; mixing 100 parts by weight of the mixed precipitate with 300 to 450 parts by weight of 90 to 99% (v/v) ethanol; allowing the mixture to stand under refrigerated conditions at a temperature of −5 to 5° C. for 40 to 55 hours to separate the mixture into a supernatant and a precipitate; and mixing the supernatant with the fifth supernatant.

More preferably, the method further include: mixing the fourth precipitate with the fifth precipitate to obtain a mixed precipitate; mixing 100 parts by weight of the mixed precipitate with 300 to 450 parts by weight of 90 to 99% (v/v) ethanol to obtain a mixture; allowing the mixture to stand under refrigerated conditions at a temperature of −5 to 5° C. for 40 to 55 hours to separated the mixture into a supernatant and a precipitate; and concentrating the supernatant at 50 to 60° C. for 60 to 95 minutes to obtain a concentrate having a Brix of 20 to 60.

The fractionation step is preferably carried out by allowing the mixture to stand for 20 to 96 hours while repeating heating and cooling cycles between −5° C. and 5° C. at time intervals of 40 to 60 minutes.

A further aspect of the present invention provides a red ginseng saponin extract prepared by the method.

According to the method of the present invention, saponin components are extracted from red ginseng in high yield and non-saponin components are efficiently removed from the extract. The red ginseng saponin extract of the present invention is free of precipitable substances and putrefactive substances, such as starch and free sugars, and contains high-purity saponin components at high concentrations. The red ginseng saponin extract of the present invention is prevented from being discolored and precipitated even after long-term storage, achieving good storage stability and high marketability.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 6 is an analytical report providing the contents of major saponin components in a first concentrate before fractionation;

FIG. 7 is an analytical report providing the contents of major saponin components in a second supernatant after fractionation;

FIGS. 8 and 9 are analytical reports providing the contents of major saponin components in a second concentrate having a Brix of 60, which was obtained by reconcentrating a supernatant after fractionation;

FIG. 10 is an analytical report providing the contents of major saponin components in a commercially available red ginseng concentrate product;

FIG. 11 is an analytical report providing the contents of major saponin components in a concentrate of a supernatant obtained by fractionating a commercially available red ginseng concentrate product;

FIG. 12 is an analytical report providing the contents of major saponin components in a second precipitate obtained after fractionation;

FIG. 13 is an analytical report providing the contents of major saponin components in a precipitate obtained after fractionation of a commercially available red ginseng concentrate product;

FIG. 14 is an analytical report providing the contents of major saponin components in a red ginseng saponin extract having a Brix of 40 prepared by purifying fourth and fifth precipitates obtained during purification with ethanol, followed by concentration; and FIG. 15 is an analytical report providing the total content of major saponin components in a beverage containing a red ginseng saponin extract of the present invention after storage for a predetermined period of time, and the pH and chromaticity coordinates of the beverage.

DETAILED DESCRIPTION OF THE INVENTION

Figure 1:
FIG. 1 is a photograph showing a second precipitate remaining after a second supernatant following fractionation was separated/removed.

The present invention provides a method for preparing a red ginseng saponin extract, including: extracting red ginseng with alkaline ionized water and ethanol to prepare a red ginseng extract; primarily precipitating the red ginseng extract under cooling to obtain a first supernatant; concentrating the first supernatant to obtain a first concentrate; mixing the first concentrate with alkaline ionized water and ethanol and secondarily precipitating the mixture under cooling to obtain a second supernatant; and concentrating the second supernatant to obtain a second concentrate. The present invention also provides a red ginseng saponin extract prepared by the method.

The method may further include purifying the second concentrate by repeating the steps of mixing the second concentrate with alkaline ionized water and precipitating the mixture under cooling to obtain a supernatant. In this case, the red ginseng saponin extract can be purified because fine suspended solids are removed from the red ginseng saponin extract. The red ginseng saponin extract may be further purified by concentrating the red ginseng saponin extract free of fine suspended solids, mixing the concentrate with ethanol, precipitating the mixture under cooling, and reconcentrating the supernatant to remaining suspended solids.

The red ginseng saponin extract may be further purified by mixing the supernatant after the purification with acidic ionized water, precipitating the mixture under cooling, and concentrating the supernatant. The method may further include recovering saponin components from the precipitates obtained during the purification.

Hereinafter, the method of the present invention will be described in detail based on the individual steps.

1) Extraction

First, red ginseng is pulverized and mixed with alkaline ionized water and ethanol as extraction solvents. The extraction solvents are used to dissolve ingredients from the red ginseng.

Alkaline ionized water is obtained by applying an electric force to general water, such as tap water or underground water. Specifically, when a direct current is applied between platinum-plated titanium anode (+) and cathode (−) immersed in water, negative ions dissolved in the water gather at the anode to generate acidic ionized water and positive ions gather at the cathode to generate alkaline ionized water.

The positive ions dissolved in the water migrate to the cathode plate. The positive ions may be, for example, calcium, magnesium, and potassium ions. The positive ions are discharged at the cathode, re-dissolved in the water, and discharged together with alkaline ionized water as cathodic electrolyzed water. Simultaneously with this, hydrogen ions ($H^+$) gain electrons ($e^-$) at the cathode to create active hydrogen. The discharged alkaline ionized water becomes alkaline and has a low oxidation-reduction potential (ORP) due to its lower hydrogen ion concentration than general water.

The alkaline ionized water contains larger amounts of healthful minerals and has smaller water molecules than general water. For these reasons, the alkaline ionized water is highly absorptive to minerals, ameliorates diarrhea and constipation, and assists in the function of the stomach. The alkaline ionized water functions to reduce harmful substances in terms of health and environment due to its ability to sterilize and disinfect.

Particularly, strongly alkaline ionized water promotes dissolution of water-soluble components from red ginseng because it can more easily dissolve proteins and fats than general solvents. Strongly alkaline ionized water eliminates oxygen free radicals, which are major causes of diseases, due to its enrichment in active hydrogen, is helpful in human health due to its enrichment in minerals, and enables efficient extraction of saponin components from red ginseng.

Water-soluble components and oil-soluble components coexist in ginseng radix saponins. Larger amounts of oil-soluble saponins are present in red ginseng than in fresh ginseng. For body absorption, saponins should cross the cell membranes to enter the cells. Oil-soluble saponins have higher permeability through the cell membranes composed of phospholipids, are much more effective in activating immune cells, and cause fewer side effects, such as fever, than water-soluble saponins.

Ethanol as the extraction solvent acts as a catalyst to dissolve red ginseng ingredients in alkaline ionized water. The use of ethanol enables extraction of both water-soluble saponins and oil-soluble saponins at low temperature without destroying the components.

For efficient extraction, red ginseng is preferably pulverized or cut into 0.5 to 2.0 cm long pieces before use. Preferably, 100 parts by weight of the red ginseng pieces are mixed with 500 to 700 parts by weight of alkaline ionized water at a pH of 10 to 12 and 1200 to 1800 parts by weight of 90 to 99% (v/v) ethanol, followed by extraction at 60 to 75° C. for 15 to 30 hours. More preferably, 100 parts by weight of the red ginseng pieces are mixed with 550 to 650 parts by weight of alkaline ionized water at a pH of 10.5 to 11.5 and 1300 to 1400 parts by weight of 93 to 97% (v/v) ethanol, followed by extraction at 60 to 75° C. for 24 to 27 hours.

If the alkaline ionized water has a pH lower than 10, the extraction temperature is lower than 60° C. or the extraction time is shorter than 15 hours, the extraction yield is lowered. Meanwhile, even though the alkaline ionized water has a pH exceeding 12, the extraction temperature exceeds 75° C. or the extraction time exceeds 30 hours, a further improvement in extraction yield is negligible, the dissolution of impurities, such as starch and free sugars, increases, and saponin components are destroyed.

If the extraction solvents are used in amounts smaller than the respective ranges defined above, the amounts of the extraction solvents remaining after absorption to the red ginseng are not sufficient to extract saponin components from the red ginseng. Meanwhile, if the extraction solvents are used in amounts larger than the respective ranges defined above, it takes an excessively long time for the subsequent concentration step to carry out. The mixing ratio of the alkaline ionized water to the ethanol is optimally determined depending on the proportions of water-soluble saponins and oil-soluble saponins in the red ginseng.

The extraction may be performed by shaking or agitating a mixture of the red ginseng, the alkaline ionized water, and the ethanol, circulating the extraction solvents in a state in which the red ginseng remains stationary, or circulating the extraction solvents while shaking or agitating the mixture.

When the extraction solvents are circulated, tiny chips of the red ginseng pieces may cause malfunction of the circulator or clog the line. In order to prevent the malfunction or clogging, it is preferred to seal the red ginseng in a cloth, such as a non-woven fabric, before extraction.

The red ginseng contains non-saponin components as well as saponin components. The non-saponin components may consist of 60 to 70% by weight of carbohydrates, such as starch, and other fibers, proteins, polysaccharides, and minerals. The red ginseng extract contains 20 to 30% of starch, 10 to 20% of free sugars, and other minerals on a dry weight basis. The contents of the components may vary depending on what kinds of extraction solvents are used or how to extract the red ginseng.

Starch present in the red ginseng extract is separated into a precipitate and a supernatant during storage. The extract having undergone layer separation during storage has low marketability. A beverage containing the extract leaves a precipitate, which lowers the marketability of the beverage.

Since starch or free sugars tend to decay with time, the extract may undergo a change in quality, such as discoloration or decay, during long-term storage.

For high marketability and storage stability, it is necessary to remove precipitable substances and putrefactive substances, such as starch and free sugars, which are non-saponin components, from the extract. To this end, the red ginseng extract is allowed to stand under refrigerated conditions at a temperature of −5 to 0° C., preferably −2 to −1° C., for 20 to 96 hours, preferably 50 to 52 hours, to precipitate non-saponin components.

When the extract is stored under refrigerated conditions, non-saponin components are precipitated by the force of gravity and solutes dissolved in the solution are precipitated by a reduction in solubility resulting from the temperature drop, enabling the removal of the non-saponin components with high efficiency.

After completion of the precipitation of the non-saponin components under cooling, the precipitate (hereinafter referred to as "first precipitate") is removed and the supernatant (hereinafter referred to as "first supernatant") is collected. At this time, it is preferred to remove oil components as impurities of the first supernatant by suitable methods, such as adsorption.

2) First Concentration

Next, the first supernatant is concentrated at 50 to 60° C., preferably 50 to 55° C., for 50 to 90 minutes, preferably 60 to 90 minutes, to obtain a first concentrate having a Brix of 55 to 65, preferably 58 to 62.

The first concentration is performed to control the composition of the first supernatant such that the subsequent fractionation step is efficiently carried out. Since the concentration temperature is lower than the boiling points of the alkaline ionized water and the ethanol as the solvents of the first supernatant, the solvents are volatilized only on the surface of the first supernatant and no noticeable vaporization takes place inside the first supernatant. Thus, saponin components dissolved in the first supernatant can be prevented from being lost together with water vapor. In addition, the concentration of the first supernatant at a low temperature can prevent saponin components from being destroyed by heat.

3) Fractionation 100 parts by weight of the first concentrate is mixed with 150 to 250 parts by weight, preferably 180 to 220 parts by weight of alkaline ionized water at a pH of 10 to 12, preferably 10.5 to 11.5, to lower the sugar content of the first concentrate to a Brix of 15 to 25, preferably 18 to 22. The mixture is mixed with 1000 to 1500 parts, preferably 1100 to 1200 parts, by weight of 90 to 99% (v/v) ethanol, preferably 93 to 97% (v/v) ethanol, to obtain a first mixture.

Next, the first mixture is allowed to stand at a temperature of −5 to 5° C. for 20 to 96 hours, and as a result, suspended solids (mainly non-saponin components) are precipitated. The first mixture is preferably allowed to stand at −3 to 3° C. for 48 to 52 hours, more preferably for 20 to 96 hours while repeating heating and cooling cycles between −5° C. and 5° C. at time intervals of 40 to 60 minutes.

Non-saponin components are precipitated by the force of gravity and a reduction in solubility resulting from the temperature drop. As the fractionation proceeds with periodically varying temperatures, aggregation of the precipitated substances is promoted, leading to an increase in the rate of precipitation.

After completion of the precipitation of the suspended solids, the precipitate (hereinafter referred to as "second precipitate") is removed and the supernatant (hereinafter referred to as "second supernatant") is collected. At this time, it is preferred to remove oil components as impurities of the second supernatant by suitable methods, such as adsorption.

4) Second Concentration

Next, the second supernatant is concentrated at 50 to 60° C., preferably 50 to 55° C., for 50 to 90 minutes, preferably for 60 to 90 minutes, to obtain a second concentrate having a Brix of 55 to 65, preferably 58 to 62.

In the second concentration step, the ethanol is slowly removed. Saponin components are prevented from being lost because the concentration temperature is lower than the boiling points of the solvents, as in the first concentration step. The fractionation and second concentration steps enable further removal of starch and free sugars from the red ginseng extract to obtain a red ginseng saponin extract with higher purity.

The red ginseng saponin extract is free of precipitable substances and putrefactive substances, such as starch and free sugars, and as a result, it is protected from being discolored and precipitated during storage. However, trace amounts of suspended solids may remain in the extract, increasing the risk that the extract may be discolored and precipitated during long-term storage.

Therefore, it is preferred to further remove impurities from the red ginseng saponin extract by purifying the second concentrate. The purification is performed by the following procedure.

5) First Purification

Alkaline ionized water is rapidly adsorbed into the body due to its small molecules. Alkaline ionized water has the ability to remove oxygen free radicals and is enriched in minerals, thus being helpful in health. For these reasons, alkaline ionized water is used for the purification of the red ginseng saponin extract.

100 parts by weight of the second concentrate is mixed with 150 to 250 parts by weight of alkaline ionized water at a pH of 10 to 12 to obtain a second mixture having a Brix of 15 to 25. Then, the second mixture is allowed to stand under refrigerated conditions at a temperature of −5 to 0° C. for 90 to 110 hours to precipitate fine suspended solids present therein. After the precipitation is finished, the precipitate (hereinafter referred to as "third precipitate") is removed and the supernatant (hereinafter referred to as "third supernatant") is collected.

Preferably, 100 parts by weight of the second concentrate is mixed with 180 to 220 parts by weight of alkaline ionized water at a pH of 10.5 to 11.5 to obtain a second mixture having a Brix of 18 to 22, which is then allowed to stand under refrigerated conditions at a temperature of −2 to −1° C. for 95 to 100 hours. This precipitation is advantageous in the removal of fine suspended solids.

Fine suspended solids present in the second concentrate are not readily precipitated due to their fine particle size. Such fine suspended solids are concentrated in the second concentration step and are then cooled in the alkaline ionized water. As a result, the fine suspended solids are deposited by an increase in the degree of saturation resulting from the concentration and a reduction in solubility resulting from the temperature drop, and the fine particles aggregate and are precipitated.

In the first purification step, lipid components, such as ceramides, are precipitated and removed from the second concentrate.

6) Second Purification 100 parts by weight of the third supernatant is mixed with 80 to 120 parts by weight of alkaline ionized water at a pH of 10 to 12 to obtain a third mixture having a Brix of 8 to 12, which is then allowed to stand under refrigerated conditions at a temperature of −5 to 0° C. for 100 to 150 hours to precipitate ultrafine suspended solids present therein. This precipitation is based on the same principle as the first purification. After the precipitation is finished, the supernatant and the precipitate (hereinafter referred to as "fourth supernatant" and "fourth precipitate", respectively) are separated from each other.

Preferably, 100 parts by weight of the third supernatant is mixed with 90 to 110 parts by weight of alkaline ionized water at a pH of 10.5 to 11.5 to obtain a third mixture having a Brix of 9 to 11, which is then allowed to stand under refrigerated conditions at a temperature of −2 to −1° C. for 110 to 130 hours. This precipitation is advantageous in the removal of ultrafine suspended solids.

The supernatant purified by the second purification has a lower Brix and contains finer suspended solids than the supernatant purified by the first purification. Thus, in the second purification step, the alkaline ionized water is mixed in a smaller amount and the mixture is allowed to stand for a longer time to remove very fine particles from the supernatant. Substances precipitated/removed from the third supernatant by the second purification are mainly proteins.

7) Third Purification 100 parts by weight of the fourth supernatant is mixed with 200 to 250 parts by weight of alkaline ionized water at a pH of 10 to 12 to obtain a fourth mixture having a Brix of 1 to 5, which is then allowed to stand under refrigerated conditions at a temperature of −5 to 0° C. for 120 to 160 hours to precipitate superfine suspended solids present therein. After the precipitation is finished, the supernatant and the precipitate (hereinafter referred to as "fifth supernatant" and "fifth precipitate", respectively) are separated from each other.

Preferably, 100 parts by weight of the fourth supernatant is mixed with 220 to 240 parts by weight of alkaline ionized water at a pH of 10.5 to 11.5 to obtain a fourth mixture having a Brix of 2 to 4, which is then allowed to stand under refrigerated conditions at a temperature of −2 to −1° C. for 130 to 150 hours. This precipitation is advantageous in the removal of superfine suspended solids.

Proteins and water-soluble components are precipitated and removed by the activation of diffusion in the third purification step.

The red ginseng saponin extract thus prepared is free of very fine suspended solids as well as precipitable substances and putrefactive substances, such as starch and free sugars. Accordingly, the red ginseng saponin extract can be prevented from being discolored and precipitated even after long-term storage.

Microbes may be included in the raw materials or may be incorporated into the raw materials during preparation and some components may remain unprecipitated or unremoved in water during purification. The microbes and the components can be removed from the red ginseng saponin extract by sterilization. The sterilization can further improve the storage stability of the red ginseng saponin extract and make the red ginseng saponin extract safe in terms of hygiene. The procedure is as follows.

8) Sterilization

The fifth supernatant is concentrated at 50 to 60° C., preferably 50 to 55° C., for 60 to 95 minutes, preferably 60 to 90 minutes, to obtain a third concentrate having a Brix of 5 to 65, preferably 18 to 22.

100 parts by weight of the third concentrate is mixed with 350 to 500 parts by weight of 90 to 99% (v/v) ethanol and is allowed to stand under refrigerated conditions at a temperature of −5 to 0° C. for 45 to 95 hours to precipitate residual suspended solids present therein, together with sterilization. After the precipitation is finished, the precipitate (hereinafter referred to as "sixth precipitate") is removed and the supernatant (hereinafter referred to as "sixth supernatant") is collected.

More preferably, 100 parts by weight of the third concentrate is mixed with 350 to 400 parts by weight of 93 to 97% (v/v) ethanol and is allowed to stand at a temperature of −2 to −1° C. for 45 to 50 hours. This precipitation under cooling is advantageous in the removal of residual suspended solids.

Next, the sixth supernatant is concentrated at 50 to 60° C., preferably 50 to 55° C., for 60 to 95 minutes, preferably 85 to 90 minutes, to obtain a fourth concentrate having a Brix of 8 to 65, preferably 58 to 62.

The sterilization of the purified red ginseng saponin extract enables the preparation of a hygienically safe composition. In addition, the ethanol can be used to precipitate and remove components remaining unprecipitated in the water in the course of the extract purification.

Non-saponin components soluble under alkaline conditions are sufficiently removed from the red ginseng saponin extract, but non-saponin components soluble under acidic conditions are not sufficiently removed and remain in the extract, resulting in the formation of a precipitate during long-term storage of the extract.

In view of this, the fifth supernatant may be further purified with acidic ionized water before the sterilization step. The purification procedure is as follows.

9) Purification with Acidic Ionized Water 100 parts by weight of the fifth supernatant is mixed with 200 to 250 parts by weight of acidic ionized water at a pH of 5 to 7 to obtain a mixture having a Brix of 1 to 5, which is then allowed to stand under refrigerated conditions at a temperature of −5 to 0° C. for 120 to 160 hours to precipitate ultrafine suspended solids present therein. After the precipitation is finished, the precipitate is removed and the supernatant is collected.

Preferably, 100 parts by weight of the fifth supernatant is mixed with 220 to 240 parts by weight of acidic ionized water at a pH of 5.5 to 6.5 to obtain a mixture having a Brix of 2 to 4, which is then allowed to stand at a temperature of −2 to −1° C. for 130 to 150 hours. This precipitation is advantageous in the removal of ultrafine suspended solids.

The purification with acidic ionized water is performed to remove non-saponins soluble under acidic conditions and is based on the phenomenon in which when non-saponin components present in the fifth supernatant are dissolved in the acidic ionized water and are then precipitated, they aggregate in the form of particles, which are precipitated/removed.

If the pH of the acidic ionized water exceeds 7, it is difficult to remove non-saponins, which are dissolved and precipitated under acidic conditions. Meanwhile, if the pH of the acidic ionized water is lower than 5, non-saponins are no longer efficiently removed and saponin components are destroyed.

When the fifth supernatant obtained after purification with the alkaline ionized water is purified with acidic ionized water, the alkaline supernatant is neutralized with the acidic supernatant. This neutralization leads to further aggregation and precipitation of the particles of suspended solids. Through the series of extraction, concentration, fractionation, purification, and sterilization steps, unwanted components, such as lipids, proteins, and water-soluble impurities, can be removed to prepare the red ginseng saponin extract in high purity.

On the other hand, after standing the fourth and fifth mixtures for a long time, some saponin components are precipitated and included in the fourth and fifth precipitates separated from the fourth and fifth supernatants, respectively. The saponin components included in the fourth and fifth precipitates are causes of low yield of saponins in the red ginseng saponin extract.

It is thus preferred to recover saponin components from the fourth and fifth precipitates. The saponin recovery can be performed by the following procedure.

10) Recovery of Saponins from the Precipitates

The fourth and fifth precipitates are collected and mixed together. 100 parts by weight of the mixed precipitate is sufficiently mixed with 300 to 450 parts by weight of 90 to 99% (v/v) ethanol and is allowed to precipitate under refrigerated conditions at a temperature of −5 to 5° C. for 40 to 55 hours. After the precipitation is finished, the precipitate is removed and the supernatant is collected.

More preferably, 100 parts by weight of the mixed precipitate is sufficiently mixed with 350 to 400 parts by weight of 93 to 97% (v/v) ethanol and is allowed to precipitate at a temperature of −2 to 5° C. for 45 to 50 hours. This precipitation under cooling is advantageous in the recovery of saponins from the precipitates.

The supernatant is collected and mixed with the fifth supernatant, followed by sterilization. As a result, the recovered saponins are included in the red ginseng saponin extract. Alternatively, the supernatant is collected and concentrated at 50 to 60° C. for 60 to 95 minutes to obtain a concentrate having a Brix of 20 to 60, which can also be used separately.

In the series of extraction, concentration, fractionation, purification, and sterilization steps, the extracts, the supernatants, the concentrates, precipitates, etc. are preferably protected from coming into contact with metal or nonferrous metal in order to inhibit changes in their physical properties. For this purpose, it is preferred that instruments, containers, etc. used in the overall procedure for the preparation of the red ginseng saponin extract are made of glass or ceramics, if possible.

The red ginseng saponin extract is substantially free of non-saponin components and contains high-purity saponin components extracted from the red ginseng. If necessary, the red ginseng saponin extract may be diluted to a Brix of 3 to 50 before use. The diluted red ginseng saponin extract can be easily utilized in many applications. The red ginseng saponin extract is prevented from being precipitated, discolored or decayed by impurities, such as starch or free sugars, even after long-term storage. Therefore, the red ginseng saponin extract has the advantages of high marketability and good storage stability.

The present invention will be explained in more detail with reference to the following examples, including test examples. These examples are provided for illustrative purposes only and are not intended to limit the present invention. It should be apparent to those skilled in the art that other substitutions and equivalents are possible without departing from the spirit or scope of the invention.

EXAMPLE 1

The tail root of six-year red ginseng was ground into 1.0-1.5 cm long pieces using a mortar and pestle and was divided into 10 small portions (each 200 g), which were put into non-woven fabric bags. Alkaline ionized water having a pH of 11.0 and an oxidation-reduction potential of −250 mV was produced using an alkaline water ionizer (LYdia8080, MAGICCOS Co. Ltd., Korea).

A 5 L water cooling hermetic circulating oil bath (SY-5-250, Zhengzhou Greatwall Scientific Industrial and Trade Co. Ltd., China) was connected to a two-layer borosilicate glass reactor (GR-50L, Zhengzhou Greatwall Scientific Industrial and Trade Co. Ltd., China) made of high borosilicate glass 3.3 and equipped with an agitator. The glass reactor was surrounded by a silicone sheet to protect from sunlight and ambient heat. The silicone sheet played a role in impact resistance and heat insulation.

After addition of 70% (v/v) ethanol to the glass reactor, the glass reactor and the oil bath were operated such that they were disinfected/sterilized. The ethanol was discharged. 12 L of alkaline ionized water at pH 11 produced using the ionizer and 34.15 L of 95% (v/v) ethanol were added to the glass reactor, and then the 10 non-woven fabric bags containing the pieces of the red ginseng tail root were added thereto.

The oil bath was operated while stirring the contents of the glass reactor by the operation of the agitator installed in the glass reactor. The operation temperature of the oil bath was set to 63.7° C. The alkaline ionized water and the ethanol were allowed to circulate between the glass reactor and the oil bath. After the temperatures of the glass reactor and the oil bath reached 63.7° C., the glass reactor was operated for additional 24 h to prepare a red ginseng extract.

The operation of the instruments was stopped. The red ginseng extract was cooled to 45° C. and maintained at room temperature for 1 h. The red ginseng extract was divided into small portions (each 5 L) and stored in a refrigerator operated at −1.5° C. After storage for 24 h, the red ginseng extract was separated into a first supernatant and a first precipitate. The first supernatant was collected. Floating oils on the surface of the first supernatant were removed using an oil-adsorbing resin.

Next, a refrigerated circulator (DLSB-20/30, Zhengzhou Greatwall Scientific Industrial and Trade Co. Ltd., China) and a Teflon circulating water jet flow vacuum pump (SHB-B95T, Zhengzhou Greatwall Scientific Industrial and Trade Co. Ltd., China) were connected to a 10 L rotary evaporator (R1010, Zhengzhou Greatwall Scientific Industrial and Trade Co. Ltd., China). In the refrigerated circulator, ethylene glycol was used as a cooling medium and the cooling temperature was set between a maximum of −10° C. and a minimum of −4° C. The vacuum pressure of the vacuum pump was set to a maximum of −0.098 MPa·G (0.003325 MPa·A) and a minimum of 0.095 MPa·G (0.006325 MPa·A).

70% (v/v) ethanol was added to the rotary evaporator. The rotary evaporator, the refrigerated circulator, and the vacuum pump were operated such that they were disinfected/sterilized. The ethanol was discharged and the oil-free supernatant was divided into small portions (each 5 L). One portion was introduced into the rotary evaporator through a 100 mesh filter and was then concentrated at 54° C. for 87° C. by the operation of the refrigerated circulator, the vacuum pump, and the rotary evaporator to obtain a first concentrate having a Brix of 60. The remaining portions of the first supernatant were concentrated in the same manner as described above.

310 g of the first concentrate was mixed with 620 ml of alkaline ionized water at pH 11 to lower the sugar content to a Brix of 20. The mixture was mixed with 4450 ml of 95% (v/v) ethanol to obtain a first mixture, which was then stored in a refrigerator at −1.5° C. for 50 h. During the storage, the first mixture was fractionated into a second supernatant and a second precipitate.

FIG. 1 is a photograph showing the second precipitate remaining after the second supernatant was separated/removed. As shown in FIG. 1, yellow suspended solids in the form of mud were settled down at the bottom. Accordingly, the second precipitate could be separated into the second supernatant even without the use of a special tool.

Next, floating oils on the surface of the second supernatant were removed using an oil-adsorbing resin. Then, the second supernatant was put in the rotary evaporator through a 100-mesh filter and reconcentrated at 54° C. for 87 min in the same manner as described above to obtain a second concentrate having a Brix of 60 as a red ginseng saponin extract.

EXAMPLE 2

Figure 2:
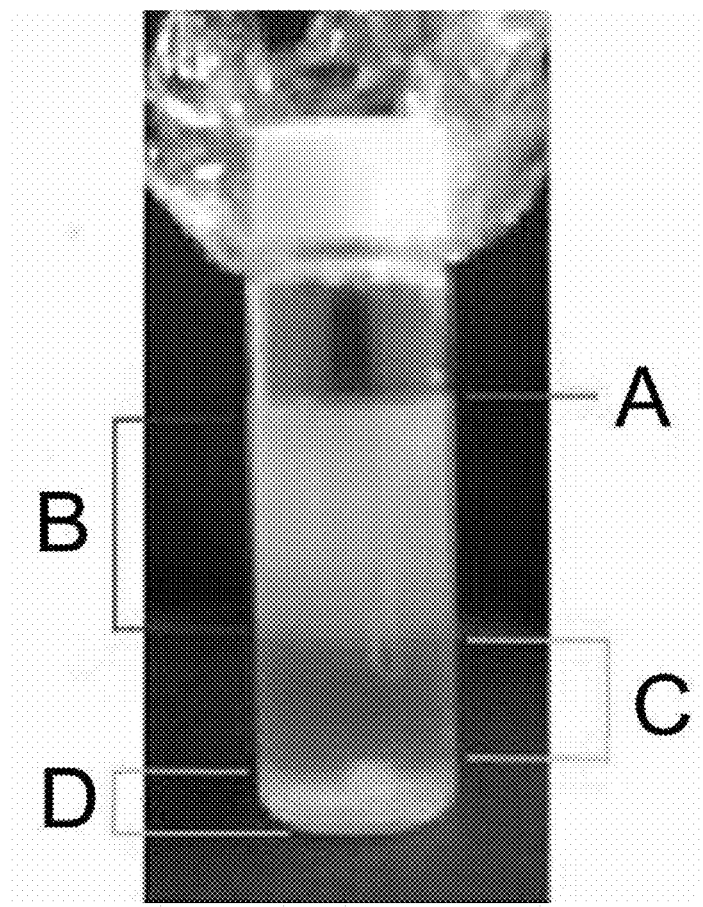
FIG. 2 is a photograph showing four separate layers of a second mixture having a Brix of 20, which was obtained by mixing a second concentrate with alkaline ionized water, after the second mixture was left standing for layer separation.

165 g of the red ginseng saponin extract prepared in Example 1 was mixed with 330 mL of alkaline ionized water at pH 11 to obtain a second mixture having a Brix of 20. The second mixture was allowed to stand at 25° C. for 48 h. As shown in FIG. 2, the second mixture was separated into an oil layer (A), a non-saponin layer (B), a saponin layer (C), and a starch layer (D). After 96 h, these layers were again combined together. This phenomenon reveals that components other than saponins remained in the red ginseng saponin extract of Example 1, requiring further purification thereof.

Figure 3:
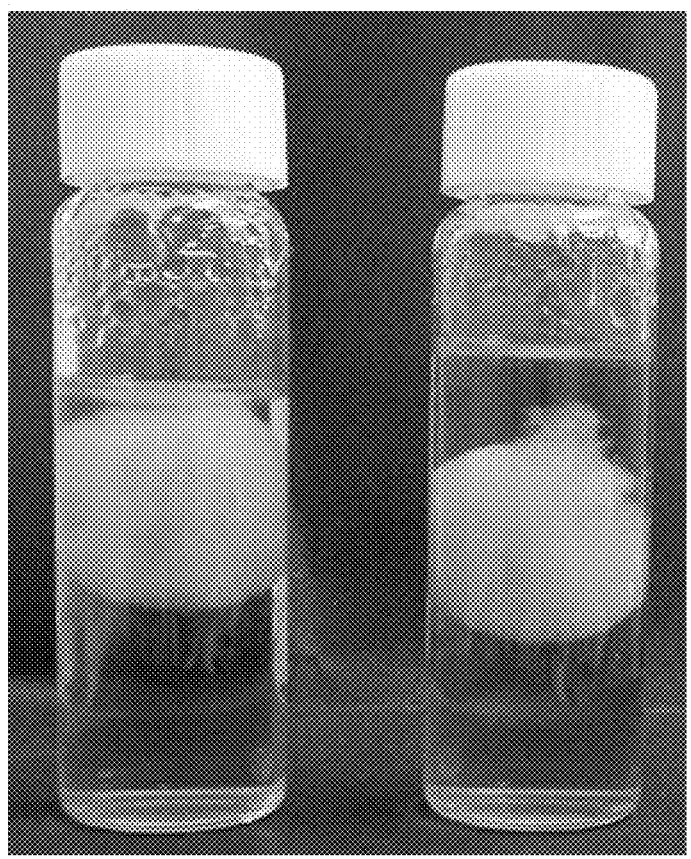
FIG. 3 shows photographs, each showing the separation of a saponin layer and a non-saponin layer of a third mixture having a Brix of 10, which was obtained by mixing a third supernatant with alkaline ionized water, after the third mixture was left standing for layer separation.

After storage in a refrigerator at −1.5° C. for 98 h, the second mixture was separated into a third supernatant and a third precipitate, which was mainly composed of lipids. Then, 250 g of the third supernatant was mixed with 250 ml of alkaline ionized water at pH 11 to obtain a third mixture having a Brix of 10. The third mixture was allowed to stand at 25° C. for 8 h. As shown in FIG. 3, a non-saponin layer still remained in the third mixture.

After storage in a refrigerator at −1.5° C. for 120 h, the third mixture was separated into a fourth supernatant and a fourth precipitate, which was mainly deep yellow and pink in color. Then, 150 g of the fourth supernatant was mixed with 345 ml of alkaline ionized water at pH 11 to obtain a fourth mixture having a Brix of 3.

The fourth mixture was allowed to stand in a refrigerator at −1.5° C. for 140 h. As a result, the fourth mixture was separated into a fifth supernatant and a fifth precipitate, which was mainly white in color. The fifth supernatant was collected as a red ginseng saponin extract.

EXAMPLE 3

Figure 4:
FIG. 4 is a photograph showing the separation of a saponin layer and a starch layer of a fifth supernatant having a Brix of 3, which had undergone purification, after the fifth supernatant was left standing for layer separation.

The fifth supernatant was left to stand at 25° C. for 8 h. As shown in FIG. 4, the starch layer still remained unremoved, demonstrating that the fine starch particles contained in the red ginseng extract were not easily removed despite the series of separation steps.

The fifth supernatant was added to the disinfected/sterilized rotary evaporator used in Example 1, followed by concentration at 54° C. for 87 min to obtain a third concentrate having a Brix of 20. 140 g of the third concentrate was mixed with 670 ml of 95% (v/v) ethanol and stored in a refrigerator at −1.5° C. for 48 h to obtain a sixth supernatant and a sixth precipitate separated from each other. Then, 250 g of the sixth supernatant was added to the disinfected/sterilized rotary evaporator and concentrated at 54° C. for 87 min to obtain a fourth concentrate having a Brix of 10 as a red ginseng saponin extract.

EXAMPLE 4

The fourth precipitate and the fifth precipitate obtained in Example 2 were mixed together. The mixed precipitate was mixed with 95% (v/v) ethanol in a ratio of 1:4. Then, the mixture was stored in a refrigerator at −1.5° C. for 48 h to obtain a supernatant and a precipitate separated from each other.

Figure 5:
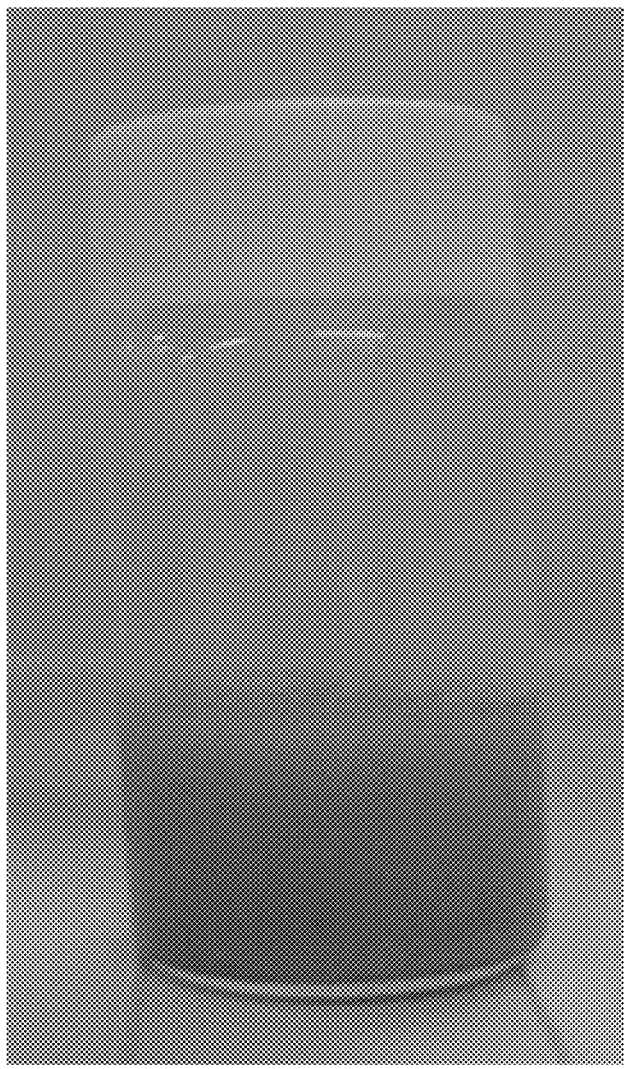
FIG. 5 is a photograph showing a red ginseng saponin extract having a Brix of 40 prepared by purifying fourth and fifth precipitates obtained during purification with ethanol, followed by concentration.

The supernatant was added to the disinfected/sterilized rotary evaporator used in Example 1, followed by concentration at 54° C. for 87 min to obtain a red ginseng saponin extract having a Brix of 20. The red ginseng saponin extract was left to stand at 25° C. for 8 h. As shown in FIG. 5, the red ginseng saponin extract did not form a precipitate and was maintained in a dispersed state.

<Test Example 1> Saponin Content Analysis

The first concentrate having a Brix of 60 obtained by concentrating the first supernatant in Example 1, the second supernatant obtained by fractionating the first concentrate, and the red ginseng saponin extract (second concentrate) having a Brix of 60 prepared by reconcentrating the second supernatant were requested for the contents of major saponins Rg1, Rb1, and Rg3 to the Biofood Technology Center, Jeonnam Bioindustry Foundation, Korea. The results are shown in FIGS. 6 to 9.

The contents of saponins Rg1, Rb1, and Rg3 in the first concentrate before fractionation were 4.0106 mg/g, 28.3127 mg/g, and 0.7982 mg/g, respectively, and the total saponin content Rg1+Rb1+Rg3 was 33.1215 mg/g, as shown in FIG. 6. In contrast, the contents of saponins Rg1, Rb1, and Rg3 in the second supernatant after fractionation were 4.4604 mg/g, 30.7846 mg/g, and 0.9290 mg/g, respectively, and the total saponin content Rg1+Rb1+Rg3 was 36.174 mg/g, as shown in FIG. 7. From these results, it can be seen that the total content of major saponin components was increased by 9.2% after fractionation.

FIG. 8 shows the contents of saponins in the second concentrate having a Brix of 60 obtained by reconcentrating the second supernatant after fractionation. The contents of saponins Rg1, Rb1, and Rg3 in the second concentrate were 4.5094 mg/g, 40.7237 mg/g, and 1.8069 mg/g, respectively, and the total saponin content Rg1+Rb1+Rg3 was 47.04 mg/g. These results reveal that the total saponin content of the second concentrate was increased by 42.0% compared to that of the first concentrate obtained by concentrating the first supernatant before fractionation.

Changes in the contents of major saponin components depending on the cooling precipitation conditions for fractionation were observed. For this observation, the 20 Brix mixture was stored for 50 h while repeating temperature cycles between −3° C. and 3° C. at time intervals of 50 min, instead of storage in a refrigerator at a constant temperature of −1.5° C. upon fractionation. As a result, the 20 Brix mixture was fractionated into a supernatant (2') and a precipitate (2').

The supernatant (2') was reconcentrated to a Brix of 60 and the contents of major saponin components therein were analyzed. The results are shown in FIG. 9. The contents of major saponin components Rg1, Rb1, and Rg3 in the supernatant (2') were found to be 4.4089 mg/g, 51.0283 mg/g, and 2.1253 mg/g, respectively, the total saponin content Rg1+Rb1+Rg3 being 57.5625 mg/g.

The analysis of the results reveal that the total content of major saponin components in the first supernatant before fractionation was increased by 73.8% compared to that in the first concentrate having a Brix of 60 obtained by concentrating the first supernatant and by 22.4% compared to that in the second concentrate having a Brix of 60 obtained by reconcentrating the second supernatant after fractionation in a refrigerator at a constant temperature of −1.5° C.

There results can lead to the conclusion that fractionation with periodic temperature variations above and below 0° C. contributes to a further improvement in the separation efficiency of saponins and non-saponins compared to fractionation under constant refrigerated conditions.

The saponin content of the second supernatant after fractionation was increased because the non-saponin components were precipitated and removed from the red ginseng extract by fractionation. This difference was clearly confirmed when the saponin content of the first supernatant before fractionation was compared with that of the second supernatant concentrated to the same Brix as the first supernatant.

To more clearly confirm the fractionation effects, a red ginseng concentrate product was purchased in the market and the contents of major saponin components therein were measured. After the red ginseng concentrate product was fractionated and reconcentrated in the same manner as in the present invention, the contents of major saponin components therein were measured. The results are shown in FIGS. 10 and 11.

As shown in FIG. 10, the contents of saponins Rg1, Rb1, and Rg3 in the red ginseng concentrate product before fractionation were 1.6242 mg/g, 4.5954 mg/g, and 0.4731 mg/g, respectively, and the total saponin content Rg1+Rb1+Rg3 was 6.6927 mg/g. In contrast, the contents of saponins Rg1, Rb1, and Rg3 in the supernatant after fractionation and reconcentration were 2.5980 mg/g, 7.0547 mg/g, and 0.7651 mg/g, respectively, and the total saponin content Rg1+Rb1+Rg3 was 10.4178 mg/g, as shown in FIG. 11. From these results, it can be seen that the total content of major saponin components was increased by 55.7% after fractionation and reconcentration.

The contents of saponin components in the precipitates were analyzed to confirm whether the saponin components were included in the precipitates and were lost. The results are shown in FIGS. 12 and 13.

FIG. 12 shows the contents of major saponin components in the second precipitate after fractionation in Example 1. No major saponin components were observed in the second precipitate. FIG. 13 shows the contents of major saponin components in the precipitate of the commercial red ginseng concentrate product after fractionation. As shown in FIG. 13, a portion of Rb1 was included in the precipitate.

This difference is thought to arise from different methods for extracting and concentrating saponin components from red ginseng by which the mixing proportions of saponin components and non-saponin components in the extracts and the proportions of non-saponin components were varied.

The contents of major saponin components in the red ginseng saponin extract prepared in Example 4 were analyzed and are shown in FIG. 14. The contents of Rg1, Rb1, and Rg3 were found to be 1.4433 mg/g, 38.3214 mg/g, and 1.7696 mg/g, respectively, the total saponin content Rg1+Rb1+Rg3 being 41.5343 mg/g. Ethanol (1.8849%) was also detected.

As can be seen from the foregoing, the contents of major saponins recovered from the fourth and fifth precipitates were lower than those in the second concentrate and were higher than those in the first concentrate before fractionation, the second supernatant after fractionation, and the commercial red ginseng concentrate product. These results suggest that saponin components can be extracted from the precipitates obtained in the course of the purification of the red ginseng saponin extract and can be commercialized.

As is apparent from the foregoing, when red ginseng is extracted with alkaline ionized water and ethanol at low temperature in accordance with the method of the present invention, large amounts of saponins dissolved from red ginseng are present in the extract. According to the method of the present invention, after the extract is precipitated under cooling, the supernatant is collected, concentrated, mixed with alkaline ionized water and ethanol, and reprecipitated under cooling. As a result, non-saponin components can be selectively precipitated/removed. Therefore, a supernatant containing high-purity saponin components can be obtained and the concentration of the supernatant can yield a red ginseng extract containing saponin components at high concentrations.

There are significant differences in the content of major saponin components between the red ginseng saponin extract of the present invention and the commercial red ginseng concentrate product. The recovery of saponin components from the precipitates, which have been discarded, leads to an increase in the extraction yield of saponins. In conclusion, the method of the present invention is more effective in extracting saponin components from red ginseng and removing non-saponin components from the extract and can extract saponin components in higher yield than the prior art.

<Test Example 2> Beverage Production

The 60 Brix red ginseng saponin extract (fourth concentrate) of Example 3 was mixed with mineral water purchased in the market to produce a beverage in which major saponin components Rg1, Rb1, and Rg3 was present in a total amount of 4.95 mg/g. After storage at 1-4° C. for 20 days, the pH and chromaticity of the beverage were measured. The results are shown in FIG. 15.

As shown in FIG. 15, the beverage was measured to have a pH of 7.527. Considering the fact that the mineral water is weakly alkaline (pH 7.6-7.7), the addition of the red ginseng saponin extract did not contribute to a significant change in the pH of the beverage. Since the pH values of all body fluids other than the gastric fluid and urine are maintained at 7.2-7.8 and the normal pH of blood and body fluids is 7.4, the pH level of the beverage containing the red ginseng saponin extract can be considered suitable as drinking water.

The beverage had color coordinates (x, y) of 0.3137 and 0.3316 on the CIE 1931 chromaticity diagram. The color coordinates represent that the beverage was colorless. No precipitates were settled down at the bottom, indicating that the beverage containing the red ginseng saponin extract did not undergo discoloration, modification or precipitation during long-term storage.

The beverage containing the red ginseng saponin extract of the present invention contains red ginseng saponins is expected to assist in the activities of endogenous enzymes and antioxidants due to the presence of saponins as healthful ingredients. Therefore, the beverage would be effective in digesting foods and achieving improved digestive absorptivity and immunity, thus being suitable as functional drinking water.

EXPLANATION OF REFERENCE NUMERALS

A: Oil layer, B: Non-saponin layer, C: Saponin layer, D: Starch layer

What is claimed is:

1. A method for increasing the saponin content of a red ginseng extract, comprising the steps of:
   (a) mixing 100 parts by weight of red ginseng with 500 to 700 parts by weight of alkaline ionized water at a pH of 10 to 12 and 1200 to 1800 parts by weight of 90 to 99% (v/v) ethanol and extracting the red ginseng at 60 to 75° C. for 15 to 30 hours to prepare a red ginseng extract;
   (b) allowing the red ginseng extract to stand at −5 to 0° C. for 20 to 96 hours to separate the red ginseng extract into a first supernatant and a first precipitate;
   (c) concentrating the first supernatant at 50 to 60° C. for 50 to 90 minutes to obtain a first concentrate having a Brix of 55 to 65;
   (d) mixing 100 parts by weight of the first concentrate with 150 to 250 parts by weight of alkaline ionized water at a pH of 10 to 12 to adjust the Brix to 15 to 25;
   (e) mixing the mixture with 1000 to 1500 parts by weight of 90 to 99% (v/v) ethanol to obtain a first mixture;
   (f) allowing the first mixture to stand at −5 to 5° C. for 20 to 96 hours to fractionate the first mixture into a second supernatant and a second precipitate; and
   (g) concentrating the second supernatant at 50 to 60° C. for 50 to 90 minutes to obtain a concentrated supernatant product having a Brix of 55-65.

2. The method according to claim 1, further comprising the steps of:
   (h) mixing 100 parts by weight of the concentrated supernatant of step (g) with 150 to 250 parts by weight of alkaline ionized water at a pH of 10 to 12 to obtain a second mixture having a Brix of 15 to 25;
   (i) allowing the second mixture to stand at −5 to 0° C. for 90 to 110 hours to separate the second mixture into a third supernatant and a third precipitate;

(j) mixing 100 parts by weight of the third supernatant with 80 to 120 parts by weight of alkaline ionized water at a pH of 10 to 12 to obtain a third mixture having a Brix of 8 to 12;

(k) allowing the third mixture to stand at −5 to 0° C. for 100 to 150 hours to separate the third mixture into a fourth supernatant and a fourth precipitate;

(l) mixing 100 parts by weight of the fourth supernatant with 200 to 250 parts by weight of alkaline ionized water at a pH of 10 to 12 to obtain a fourth mixture having a Brix of 1 to 5; and (m) allowing the fourth mixture to stand at −5 to 0° C. for 120 to 160 hours to separate the fourth mixture into a fifth supernatant and a fifth precipitate and collecting the fifth supernatant.

3. The method according to claim 2, further comprising the steps of:

(n) concentrating the fifth supernatant at 50 to 60° C. for 60 to 95 minutes to obtain a third concentrate having a Brix of 5 to 65;

(o) mixing 100 parts by weight of the third concentrate with 350 to 500 parts by weight of 90 to 99% (v/v) ethanol and allowing the mixture at −5 to 0° C. for 45 to 95 hours to separate the mixture into a sixth supernatant and a sixth precipitate; and (p) concentrating the sixth supernatant at 50 to 60° C. for 60 to 95 minutes to obtain a fourth concentrate having a Brix of 8 to 65.

4. The method according to claim 3, wherein the third concentrate is obtained by mixing 100 parts by weight of the fifth supernatant with 200 to 250 parts by weight of acidic ionized water at a pH of 5 to 7 to obtain a mixture having a Brix of 1 to 5, allowing the mixture to stand at −5 to 0° C. for 120 to 160 hours to separate the mixture into a supernatant and a precipitate, removing the precipitate, and concentrating the supernatant.

5. The method according to claim 3, further comprising the steps of:

(q) mixing the fourth precipitate with the fifth precipitate to obtain a mixed precipitate;

(r) mixing 100 parts by weight of the mixed precipitate with 300 to 450 parts by weight of 90 to 99% (v/v) ethanol;

(s) allowing the mixture to stand under refrigerated conditions at a temperature of −5 to 5° C. for 40 to 55 hours to separate the mixture into a supernatant and a precipitate; and (t) mixing the supernatant with the fifth supernatant.

6. The method according to claim 2, further comprising the steps of:

(n) mixing the fourth precipitate with the fifth precipitate to obtain a mixed precipitate;

(o) mixing 100 parts by weight of the mixed precipitate with 300 to 450 parts by weight of 90 to 99% (v/v) ethanol to obtain a mixture;

(p) allowing the mixture to stand under refrigerated conditions at a temperature of −5 to 5° C. for 40 to 55 hours to separate the mixture into a supernatant and a precipitate; and (q) concentrating the supernatant at 50 to 60° C. for 60 to 95 minutes to obtain a concentrate having a Brix of 20 to 60.

7. The method according to claim 1, wherein the fractionation step (f) is carried out by allowing the mixture to stand for 20 to 96 hours while repeating heating and cooling cycles between −5° C. and 5° C. at time intervals of 40 to 60 minutes.

* * * * *